United States Patent [19]

Kaniadakis

[11] Patent Number: 4,512,739
[45] Date of Patent: Apr. 23, 1985

[54] ORTHODONTIC RUBBER BAND APPLICATOR

[76] Inventor: Steven J. Kaniadakis, Tierra Verde Island, Tierra Verde, Fla. 33715

[21] Appl. No.: 540,321

[22] Filed: Oct. 11, 1983

[51] Int. Cl.³ .............................................. A61C 3/00
[52] U.S. Cl. ........................................ 433/3; 433/141
[58] Field of Search .................................. 433/3, 141

[56] References Cited

U.S. PATENT DOCUMENTS

| | | | |
|---|---|---|---|
| 3,475,818 | 11/1969 | Abrams | 433/3 |
| 3,861,045 | 1/1975 | Canter et al. | 433/3 |
| 4,001,940 | 1/1977 | Cusato | 433/3 |
| 4,127,940 | 12/1978 | Shilliday | 433/3 |
| 4,330,271 | 5/1982 | Anderson | 433/3 |

Primary Examiner—John J. Wilson
Attorney, Agent, or Firm—Ronald E. Smith

[57] ABSTRACT

An orthodontic instrument designed for use by patients. An elongate rod has a greater-than-180 degree bend formed in its medial portion so that the opposite ends of the rod are disposed in coplanar, transversely spaced apart relation to one another at the part of the instrument that is opposite its medial portion. The bend is slightly greater than 180 degrees so that a first, or upper arm is obliquely disposed relative to the second, or lower arm of the instrument. The distal end of the first arm is bent upwardly about 45 degrees from the horizontal and the respective distal ends of the rod are provided with annular grooves to receive opposite ends of rubber bands of the type commonly used in orthodontics. The device is held in a vertical or horizontal plane when in use, and its flat profile enables the rubber bands to be applied and removed to and from hooks when the device is held in parallel or perpendicular relation to the surface of the tooth with which the respective hooks are associated.

4 Claims, 3 Drawing Figures

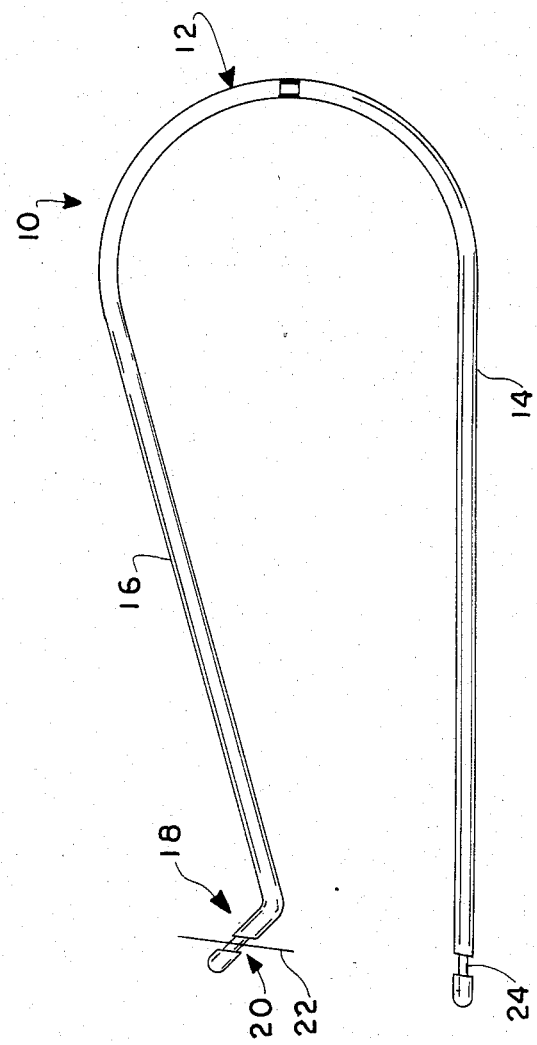
FIG_1

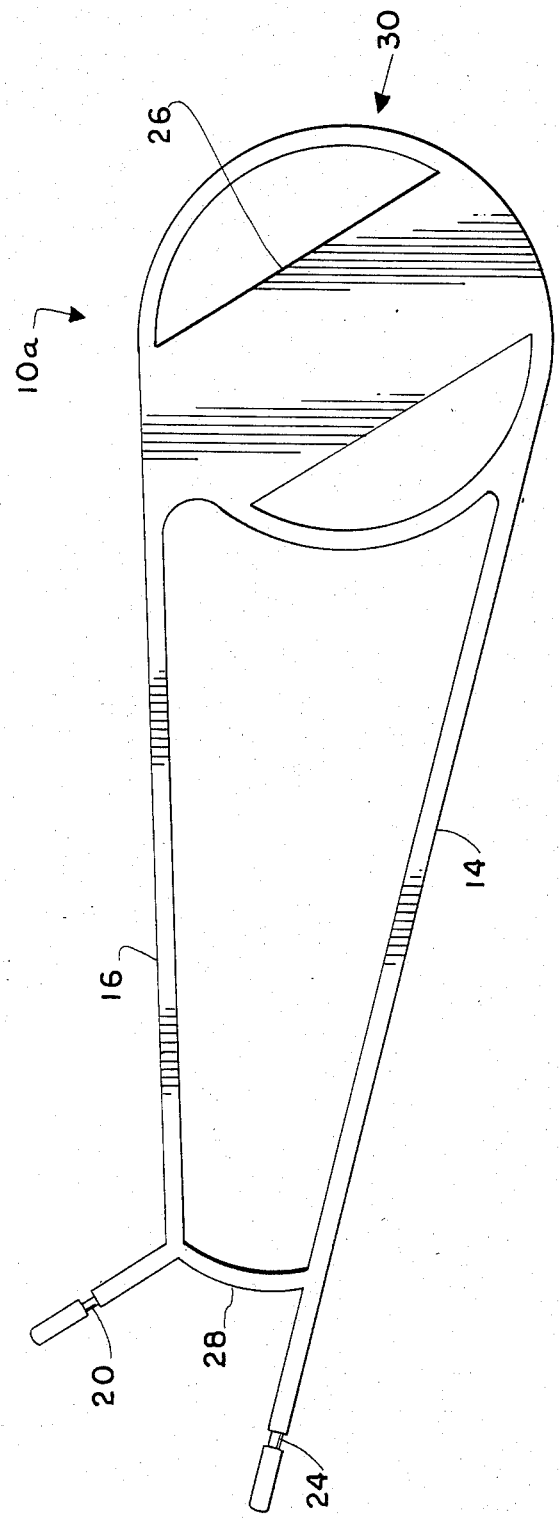
FIG_2

FIG_3
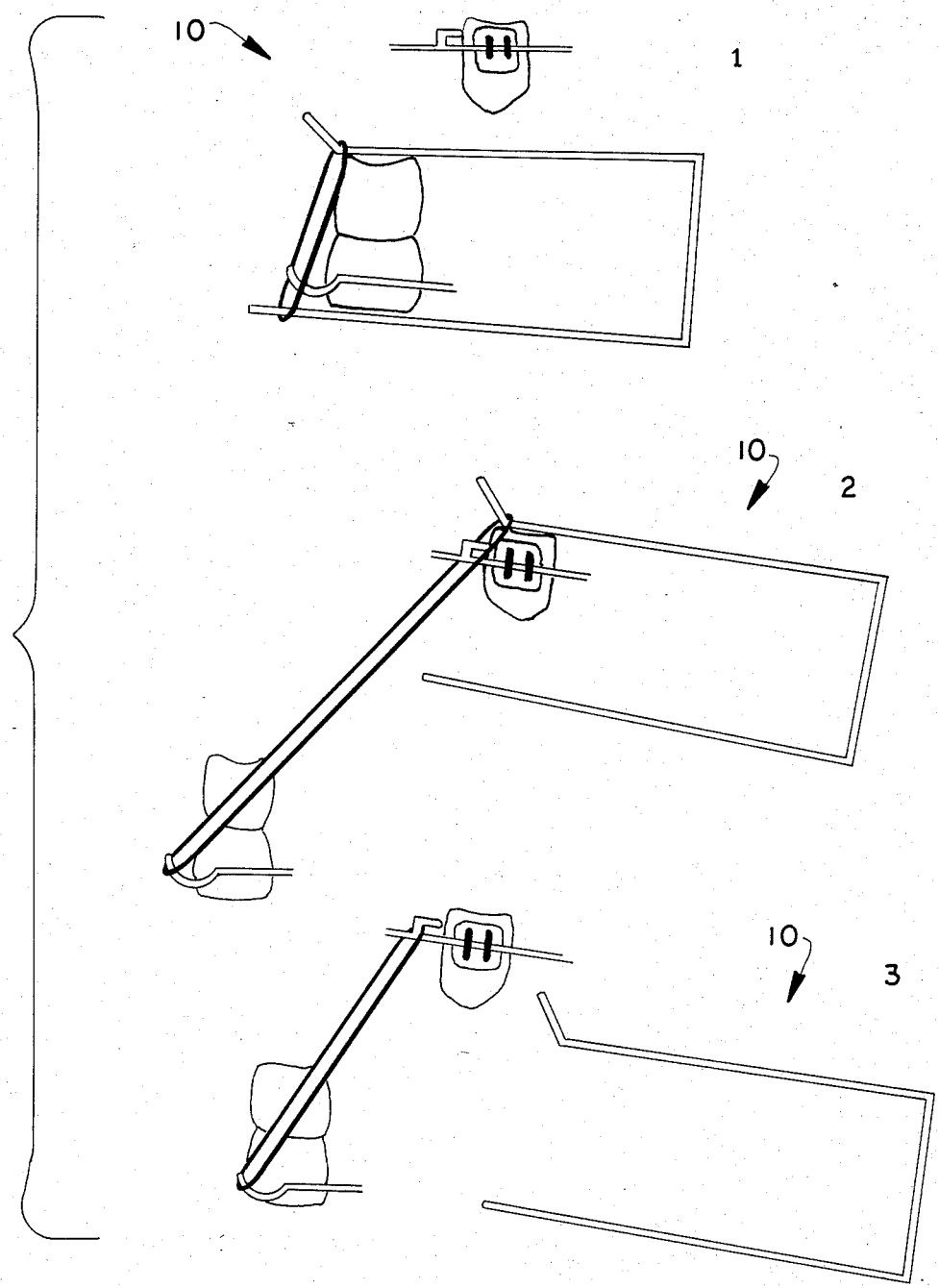

ORTHODONTIC RUBBER BAND APPLICATOR

BACKGROUND OF THE INVENTION

1. Field of the Invention

This invention relates, generally, to implements of the type used in orthodontics for placing rubber bands on dental braces, and removing the same therefrom, and more specifically relates to an implement designed for use by patients.

2. Description of the Prior Art

A patentability search that was conducted prior to the filing of this disclosure located the following U.S. patents in the general field of this invention:

| Patentee | U.S. Pat. No. | Date of Issue |
|---|---|---|
| Abrams | 3,475,818 | 11-04-69 |
| Canter et al. | 3,861,045 | 01-21-75 |
| Cusato | 4,001,940 | 01-11-77 |
| Shilliday | 4,127,940 | 12-05-78 |
| Anderson | 4,330,271 | 05-18-82 |

The Cusado, Shilliday and Anderson disclosures show devices specifically designed for use by orthodontists, not their patients. Moreover, Abrams and Cusado show devices designed for the application phase of the rubber band to arch wire-applying process, and thus such devices are not advantageously employed in the context of removing such bands. Another drawback of the earlier devices is that they have utility primarily in applying rubber bands in what is known as the "Class two" position, and thus may not be advantageously used in other contexts.

Perhaps the most important limitation of the prior art devices, however, is their inability to pass what is known as a "pharynx choke tube test" wherein a tube having a diameter corresponding to the diameter of the human pharynx is employed. Objects capable of entering the tube are unacceptable for use by consumers. Some of the devices of the prior art cannot only enter the human pharynx but are actually designed such that a mis-handling of the same could sling the device into the pharynx as a projectile where it could subsequently be asperated by the patient (note the Abrams and Canter devices, e.g.). The Abrams device could even inflict trauma on the gums and delicate mucosal membranes if not used with the utmost caution.

There is a clear need for a safe yet inexpensive device for applying and removing rubber bands to the hooks on orthodontic braces. The ideal device would be easy to use in the patient's own domain whether such domain be at home, school, or place of employment. The ideal device would be easy to use by the patient in the absence of complicated twisting movements, would not necessarily require the use of a mirror, and could be used for practically any type of rubber band position found in orthodontic treatments. Although the art is replete with attempts to provide the ideal instrument, the needed device does not appear therein.

SUMMARY OF THE INVENTION

The longstanding but heretofore unfulfilled need for a device that overcomes the limitations of the prior art is now provided in the form of a slimline, lightweight implement which safely passes the aforementioned consumer pharynx choke tube test and which has no parts that can injure a patient's gums.

Superior features of the inventive device described hereinafter are believed to be significant in numerous ways. For example, orthodontics patients are required to apply and remove their rubber bands several times every day, day in and day out, while they are undergoing treatment, and the treatment normally lasts for an extended period of time.

An elongate, preferably plastic, rod is bent gently at its medial portion to produce a pair of obliquely coplanar arm members that are integrally formed with one another via said bent intermediate portion. The bend is greater than 180 degrees so that the arms converge relative to one another. The respective distal ends of the arms are provided with annular grooves for the transient reception of rubber bands of any type commonly employed in orthodontic braces. A first, or upper arm has a 45 degree band, relative to the horizontal, formed adjacent its distal end, and the aforesaid groove formed therein is inclined about seven degrees from the vertical. The groove formed in the second, or lower arm is similarly tilted about seven degrees from the vertical so that both grooves cooperate to align a rubber band looped thereabout at such angle from the vertical. Since the upper and lower arms are coplanar, it is a simple matter to hold the device in a vertical or horizontal plane when it is desired to either apply rubber bands to the hooks formed on the orthodontic braces, or to remove previously applied rubber bands from such hooks. When the bands are being applied or removed, the patient holds the instrument in a vertical or horizontal plane and positioned in a plane substantially parallel or perpendicular to the plane of the tooth associated with the particular hook with which the band is or is to be associated. Opposite ends of a rubber band are disposed in the before-mentioned grooves formed at the respective distal ends of said upper and lower arms, thereby holding the band in an open configuration. Thus, for example, when the implement is aligned in a vertical plane that is parallel to the plane of the tooth, the plane of the open rubber band will be perpendicular or normal to the plane of the tooth. This greatly facilitates the engagement of the band with the hook, or the disengagement thereof.

The aforementioned forty five degree bend is a superior feature of this invention. The bend allows the placement of a rubber band to reach a preselected hook more readily when the same is being applied thereto. The bend also assists the patient in removing the rubber band because it can reach between the rubber band structure itself thereby helping to disconnect the same therefrom.

It is therefore seen that the primary object of this invention is to provide a safe and easy-to-use device to apply to or remove rubber bands from orthodontic braces, for practically any position of said rubber bands.

A closely related object is to provide such a device that is easy to use by orthodontic patients so that the same may be given by orthodontists to their patients at the time orthodontic braces are installed or when said treatment of rubber bands is employed with orthodontic appliances.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1 is a side elevational view of a first embodiment of the invention.

FIG. 2 is a side elevational view of a second embodiment of the invention.

FIG. 3 sequentially depicts the application of a rubber band with the inventive device in one of the several environments within which the inventive device has utility.

Similar reference numerals refer to similar parts throughout the several views of the drawings.

DETAILED DESCRIPTION OF THE PREFERRED EMBODIMENT

Referring now to FIG. 1 it will there be seen that the preferred embodiment of the invention is designated by the reference numeral 10 as a whole. The device 10 is a rod-like member that is preferably formed of an FDA-approved plastic, since it is inserted into the mouth when it is being used.

The inventive instrument complies with the Food, Drug and Cosmetics Acts, specifically Title 21 of the United States Code, Sections 301–392. Its components comply with Title 21 of the Code of Federal Regulations, Chapter 1, parts 73, 74 and 81, all subparts thereof and/or subchapter B of the same, 175 subpart C section 175.300 or part 182 subchapter B of the same. These regulations include the regulation of personal hygiene products and materials used by professionals or consumers.

The device 10 is an integrally formed member having a medial portion 12 with a gentle curve formed therein as shown, a lower arm 14 that is generally horizontally disposed as shown in the drawing when the device is in use, and an upper arm 16 lying in a vertical plane that includes the lower arm 14, said upper arm 16 being disposed obliquely relative to arm 14 as a function of the greater-then-180 degree bend of the medial portion 12. The curvature of bend 12, which forms a circular configuration, enables the inventive device to pass the aforementioned consumer pharynx choke tube test.

The distal end 18 of upper arm 16 is bent at a 45 degree angle relative to the horizontal as shown, and has an annular groove 20 formed therein. The groove 20 has its axis of symmetry 22 inclined about 7 degrees from the vertical, preferably. Such orientation aligns groove 20 with a similarly inclined groove 24 formed in the distal end of the lower arm 14.

A rubber band—not shown—is thus maintained in its open configuration by disposing its diametrically opposed ends into the grooves 20, 24, which placement orients such band at the aforesaid angular orientation from the vertical.

An alternate embodiment of the inventive implement is shown in FIG. 2 and is designated 10a as a whole. Cross members or structural struts 26, 28 facilitate the gripping of the device and maintain the spacing between the upper and lower arms, respectively.

The inventive method for applying and removing rubber bands to and from orthodontic hooks is the same irrespective of the particular embodiment of the inventive concept that is employed, and will now be described.

The proximal end 30 of the device is held by a grasp similar to the grasp commonly employed in gripping a pencil. The device, with the rubber band stretched and looped about the distal ends of the respective upper and lower arms, by placing the same in grooves 20, 24 as aforesaid, is oriented to lie in a vertical plane. If a band is to interconnect upper and lower orthodontic hooks, the band is made to engage the lower hook first, preferably. Such engagement is facilitated if the device 10 is held in a plane parallel to the plane of the tooth associated with such hook, because such an orientation will place the band in a plane normal to the plane of the tooth and facilitate the hooking operation. Upon successful engagement of the band and the preselected lower hook, the band is stretched further by pulling its upper end, i.e., the portion thereof in groove 20, toward a second preselected upper hook (typically). During the hooking procedure, the device 10 is held in one hand. This leaves the other hand of the patient free. Accordingly, when the rubber band has been successfully hooked on a lower hook, and is being stretched toward an upper hook, the patient's index finger is pressed firmly against the band and the upper tooth with which the upper hook is associated. This particular step of the method may be employed in all situations, but is especially convenient for patients having hooks in a position known to orthodontists as the "class two" position. A patient then hooks the band onto the upper hook in essentially the same manner as the lower hook was engaged. The patient makes a circular motion going around the upper hook by pulling the tool 10 past the top of the hook and then backtracking across the bottom of the hook. To conclude the application, the patient pulls the instrument downward to disengage the rubber band from the groove 20. It should be understood that the particular method just described is just one example of the methods made possible by the inventive device. The invention is not limited to situations where the hooks are deployed in the Class two position, and may be employed in situations involving practically any arrangement or configuration of rubber bands.

Of course, as already emphasized, the rubber bands are not always deployed in the class two configuration. Due to the structural simplicity of the novel instrument 10, however, it will be readily apparent to the orthodontic patient how to use the invention in other situations. For example, the instrument may be held in a horizontal plane as well as in a vertical plane, and may be aligned parallel to or perpendicular to a tooth, as aforesaid, depending upon the actual deployment of the rubber bands and depending upon whether the bands are being installed or removed.

Moreover, the device can be utilized in the oral cavity proper or in the oral vestibule (when the patient's hooks lie within the arches of the teeth). When the instrument is being held parallel to the teeth, it will be disposed in the area between the teeth and buccae or cheeks. When the instrument is being held perpendicular to the teeth, its open end will be directed toward the glossopalatine and pharyngopalatine arches.

Regardless of which position the rubber bands may be deployed, class two or otherwise, orthodontists can demonstrate the inventive method to their patients quickly and efficiently, and such demonstration will be all of the instruction that the orthodontists need to make prior to sending the patient home with the implement 10 or 10a.

It will thus be seen that the objects set forth above, and those made apparent by the preceding description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

That which is claimed is:

1. A hand device of the type designed to facilitate yielding interconnection of upper and lower sets of orthodontic braces, or yielding intraconnections within upper or lower sets, by means of rubber band members, wherein the improvement comprises, an elongate rod-like member having a bend formed substantially midlength thereof, said bend being greater than 180 degrees so that a first arm member is obliquely disposed relative to a second arm member that is oriented in a generally horizontal plane when the device is in use, said first and second arm members lying in a common vertical plane when said device is oriented for use, said first arm member having a substantially 45-degree bend formed adjacent its distal end so that said distal end is disposed in diverging relation to the unbent distal end of said second arm member, the respective distal ends of said first and second arm members having cooperatively positioned annular rubber band receiving groove means formed therein to maintain a rubber band in its open configuration when diametrically opposed portions thereof are engaged in said respective groove means.

2. The device of claim 1, wherein said groove means are inclined about 5-10 degrees from the vertical so that the open band is oriented at such inclination when the device is in use.

3. The device of claim 2, wherein a first cross member is disposed in interconnecting relation to the upper and lower arm members adjacent the respective distal free ends thereof to maintain said distal ends in a predetermined spaced relation to one another.

4. The device of claim 3, wherein a second cross member is disposed in interconnecting relation to the upper and lower arm members adjacent the proximal ends thereof to maintain said arm members in a predetermined spaced relation to one another and to facilitate the gripping of the device at said proximal end.

* * * * *